United States Patent [19]

Sasaki

[11] Patent Number: 4,896,676
[45] Date of Patent: Jan. 30, 1990

[54] BLOOD PRESSURE MEASURING UNIT

[75] Inventor: Kitoh Sasaki, Tokyo, Japan

[73] Assignee: Signal Technology Co., Ltd., Tokyo, Japan

[21] Appl. No.: 263,989

[22] Filed: Oct. 27, 1988

Related U.S. Application Data

[63] Continuation of Ser. No. 32,534, Apr. 1, 1987, abandoned.

[30] Foreign Application Priority Data

Jun. 11, 1986 [JP] Japan ................................ 61-135606

[51] Int. Cl.⁴ .............................................. A61B 5/02
[52] U.S. Cl. ...................................................... 128/681
[58] Field of Search ................................ 128/637–640, 128/677–683

[56] References Cited

U.S. PATENT DOCUMENTS

| | | | |
|---|---|---|---|
| 2,753,863 | 7/1956 | Bailey | 128/686 X |
| 4,185,621 | 1/1980 | Morrow | 128/672 |
| 4,202,347 | 5/1980 | Sacks | 128/686 X |
| 4,331,154 | 5/1982 | Broadwater et al. | 128/690 X |
| 4,469,107 | 9/1984 | Asmar et al. | 128/690 X |
| 4,479,070 | 10/1984 | Frische et al. | 73/703 X |
| 4,549,550 | 10/1985 | Kani | 128/686 |
| 4,625,560 | 12/1986 | Sander | 73/718 O |
| 4,689,999 | 9/1987 | Shkedi | 73/718 X |

FOREIGN PATENT DOCUMENTS

| | | | |
|---|---|---|---|
| 2343183 | 8/1973 | Fed. Rep. of Germany | 128/686 |
| 2910302 | 3/1979 | Fed. Rep. of Germany | 128/690 |
| 2809320 | 10/1979 | Fed. Rep. of Germany | 128/686 |
| 58731 | 6/1981 | Japan . | |

OTHER PUBLICATIONS

Geddes, L. A., "The Direct and Indirect Measurement of Blood Pressure".

Primary Examiner—Francis Jaworski
Attorney, Agent, or Firm—Cushman, Darby & Cushman

[57] ABSTRACT

Disclosed is a blood pressure measuring unit comprising a casing having a wrist band to be wound around a user's wrist. The casing is installed therein with a digital display device and a blood pressure measuring device, and is provided with an air pressure chamber to which cuffs are fixed in such a manner that the cuffs are communicated with the air pressure chamber. The blood pressure measuring device is composed of a pressure sensor having a pressure sensing portion, an oscillating circuit, and a processor, the pressure sensing portion being slightly allowed to project into the air pressure chamber, and the processor being electrically connected to the digital display device.

8 Claims, 4 Drawing Sheets

BLOOD PRESSURE MEASURING UNIT

This is a continuation of application Ser. No. 032,534, filed Apr. 1, 1987 which was abandoned upon filing thereof.

BACKGROUND OF THE INVENTION:

1. FIELD OF THE INVENTION

This invention relates to a blood pressure measuring unit and, more particularly, to a blood pressure measuring unit into which a blood pressure measuring system and a wrist watch system are incorporated in the form of one integral unit.

2. DESCRIPTION OF THE PRIOR ART

Conventionally, a wrist watch has a watch casing to which is equipped a wrist band for fitting around the wrist, and, on the other hand, within which is received a watch system. It includes an analog type, a digital type, and an analog/digital type in which both said types are concurrently used.

A blood pressure meter has a wide cuff used to be wound around the upper part of an arm, the cuff being connected, on one hand, with a pump via a tube and, on the other hand, with an analog type pressure meter via another tube. A blood pressure meter of digital type also is known, which, however, is the same as the one of analog type in that it has a cuff of broad width. This blood pressure meter has a size which is as large as the size of an ordinary book.

Needless to say, a wrist watch into which such a blood pressure meter is incorporated is not known. That is to say, a prior art blood pressure meter is not a portable type which can be carried by a user while he has it with himself. It is much less possible to incorporate such a blood pressure meter into a wrist watch to make it integral with the latter.

Generally, it is preferable that the blood pressure meter can be used even at a rest interval during the working hours, or in the course of a trip. The prior art blood pressure meter, however, is inconvenient for a user to carry with himself, and, in addition, is also inconvenient to handle because of its size being large.

SUMMARY OF THE INVENTION

The present invention has been developed under the above-mentioned actual circumstances and its object is to provide a blood pressure measuring unit serving concurrently as a wrist watch, which includes a casing shaped like the casing of a wrist watch, within which a blood pressure measuring system is housed in a state wherein the same is made integral with a time-counting system of the wrist watch, thereby making the unit very convenient for a user to carry with himself and permitting the easy measuring of his blood pressure anywhere he likes.

To attain the above object, according to one aspect of the present invention, there is provided a blood pressure measuring unit comprising a casing having a wrist band to be wound around a wrist, the casing being installed therein with a digital display device and a blood pressure measuring device, and being provided with an air pressure chamber having fixed thereto cuffs in such a manner as to permit the cuffs to communicate with the air pressure chamber, the blood pressure measuring device being composed of a pressure sensor having a pressure sensing portion, an oscillating circuit, and a processor, the pressure sensing portion being slightly allowed to project into the air pressure chamber, the processor being electrically connected to the digital display device.

According to another aspect of the present invention, said digital display device preferably is substituted for by a digital watch device.

The blood pressure measuring unit according to the present invention is only slightly larger in size of casing than an ordinary wrist watch. It therefore is a compact-sized portable type which can be worn, by means of the wrist band, on a user's wrist as in the case of a wrist watch, and which is therefore convenient for the user to carry with him.

By wearing the wrist band on a user's wrist, the air in the cuffs is allowed to communicate with the air in the air pressure chamber, whereby the air in the cuffs is intermittently pressurized due to the pulsatory motion of blood vessels in the user's wrist, so that the air pressure in the air pressure chamber varies. The variation in pressure of the air pressure chamber is sensed by the pressure sensor. The detection signals of the pressure sensor are converted into digital signals by operation of the oscillating circuit, which are calculated on the basis of the data set beforehand in the processor, into blood pressure measurements, which are digitally displayed by the digital display device. A digital timepiece device may be used as such digital display device. In this case, the blood pressure measuring unit serves concurrently as a wrist watch as well.

DESCRIPTION OF THE PREFERRED EMBODIMENTS

Figure 1:
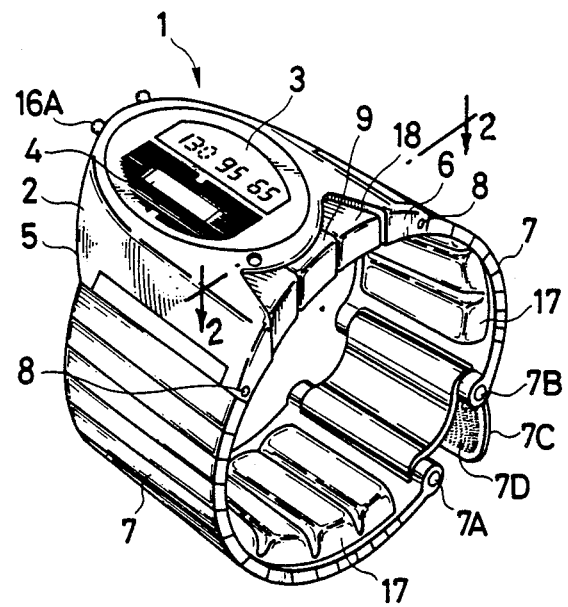
FIG. 1 is a perspective view of a blood pressure measuring unit.
Figure 2:
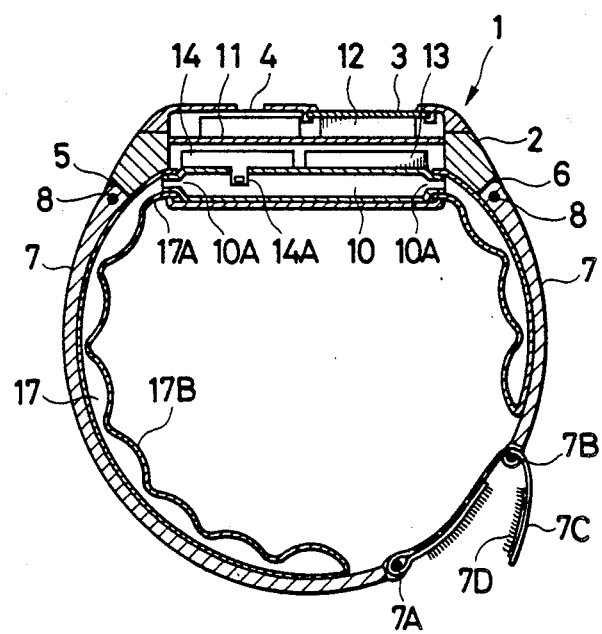
FIG. 2 is a sectional view of the blood pressure measuring unit.

An embodiment of the present invention will now be described with reference to the drawings. FIG. 1 is a perspective view of a blood pressure measuring unit according to the invention. FIG. 2 is a sectional view thereof.

Referring now to FIGS. 1 and 2, a blood pressure measuring unit 1 has a casing 2 shaped like a casing of a wrist watch, the casing being located on the same side as in the case of the wrist watch. On the top surface of the casing 2 is provided a digital display section 3 in such a manner that the upper surface thereof is directed and protruded upwards. Reference numeral 4 denotes a name display section.

At both ends of the casing 2 are formed band-fixing portions 5, 6, respectively, on which respective furthest ends of wrist bands 7, 7 are mounted by way of pin shafts 8, 8, respectively.

At a side of the casing 2 is equipped a pump 9 in a manner that it is allowed to communicate with an air pressure chamber 10 to be subsequently described.

Within the casing 2, the air pressure chamber 10 is provided at the bottom part thereof. At the upper part of the interior of the casing 2 is disposed a partitioning plate 11, on which a digital display device 12 is installed. A digital timepiece device is used for such digital display device 12 in a manner that the digital display section 3 is located on the top of the digital timepiece device.

Between the partitioning plate 11 and the air pressure chamber 10 is installed a blood pressure measuring device 13, which is composed of a pressure sensor 14 for measuring the air pressure in the air pressure chamber 10, an oscillating circuit 15 for converting the pressure measurements supplied from the pressure sensor into digital signals, and a processor 16 for comparing the digital signals supplied from the oscillating circuit 15 and conducting necessary computations into numeric blood pressure measurements. The pressure sensor 14 has a pressure sensing portion 14A which is slightly allowed to project into the air pressure chamber. The processor 16 is electrically connected to the digital display device 12.

The air pressure chamber 10 is in the shape of a tank and may be formed of metal, synthetic resin or the like. Further, it may be also in the shape of a tubular body. In the embodiment of FIG. 2, the air pressure chamber 10 is in the shape of a tank formed at its ends with openings 10A, 10A which are mounted with a tubular cuff 17 having raised portions 17B in such a manner as to permit the air in the chamber 10 to communicate with the air in the cuff. Each cuff 17 is shaped like a thin tubular body made of a resilient synthetic resin, and has an opening 17A at one longitudinal end thereof, the opening 17A being fitted over the corresponding opening 10A of the air pressure chamber 10. One surface of the cuff 17 is flat and this flat surface is mounted on an inner surface of the wrist band. On the other hand, the surface of the cuff being brought into contact with an arm is formed with a plurality of resilient elevated portions 17B. The reason for this is for the purpose of, even when the wrist band has been made annular, preventing the cuff from being bent to divide the internal air thereof into two sections, as well as for the purpose of facilitating the coherence of the cuff surface to the skin of a wrist.

In this embodiment, the surface of contact of the cuff 17 with the inner surface of the wrist band 7 has been applied with an adhesive to bond them together. Where the wrist band 7 is a metal band, however, fixing metal pins for example may be used for fixing one to the other of the two.

In FIGS. 1 and 2, the opposing ends of the wrist bands 7, 7 are mounted with pin shafts 7A, 7B, respectively, one of which is mounted with one end of an adjusting band 7C, on the outer surface of which are mounted cloth fasteners 7D. Thus, by bringing the other end of the adjusting band 7C into engagement with the other pin shaft 7B through turning it around the latter from inside and thereby bringing an outside one of the cloth fasteners into engagement with the other inside one, it is possible to fix the wrist bands 7, 7 onto the arm.

Figure 3:
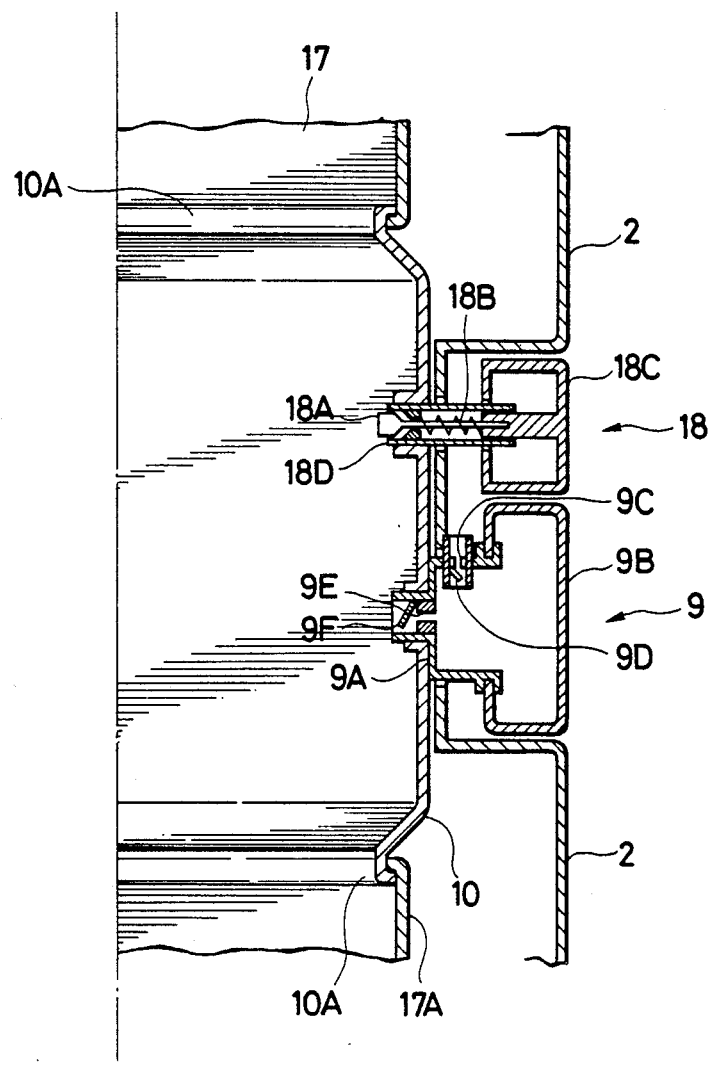
FIG. 3 is an enlarged sectional view taken along lines 3—3 in FIG. 1. illustrating the association of an air pressure chamber with a pump in the blood pressure measuring unit.

FIG. 3 is a plan view of an essential part of the blood pressure measuring unit including the air pressure chamber 10 and the pump 9 for causing air to enter the same, showing the association between the two. The pump 9 has a valve section 9A to which is equipped an air bag 9B shaped like a dome and made of synthetic resin. The valve section 9A has a suction opening 9C to which is equipped an air suction valve 9D. The valve section 9A also has a discharge opening 9E to which is equipped an air discharge valve 9F. Thus, when the air bag 9B is pressurized from outside, air already sucked therein by way of the suction opening 9C is discharged into the air pressure chamber 10 by way of the discharge opening 9E. This discharge opening 9E is formed into a small thin pipe which is fitted into a corresponding wall of the air pressure chamber 10 so as to allow the communication between the air bag 9B and the air pressure chamber 10. Namely, by pressurizing the air bag 9B, the air sucked via the suction opening 9C is discharged into the air pressure chamber 10 via the discharge opening 9E. By repeating this operation, air is sent into the air pressure chamber 10 and the cuffs 17, 17 communicated therewith to thereby cause an increase in the internal pressure thereof.

In FIG. 3, a reference numeral 18 denotes a discharge valve for drawing off the air in the air pressure chamber 10. The discharge valve 18 has a valve rod unit 18A and a spring 18B for urging the valve rod 18A outwardly of the air pressure chamber 10, whereby the pushing of a head portion 18C of the valve rod unit 18A toward the air pressure chamber 10 moves the valve rod unit 18A toward the chamber 10 against the urging force of the spring 18B to make open a discharge opening 18D.

Figure 4:
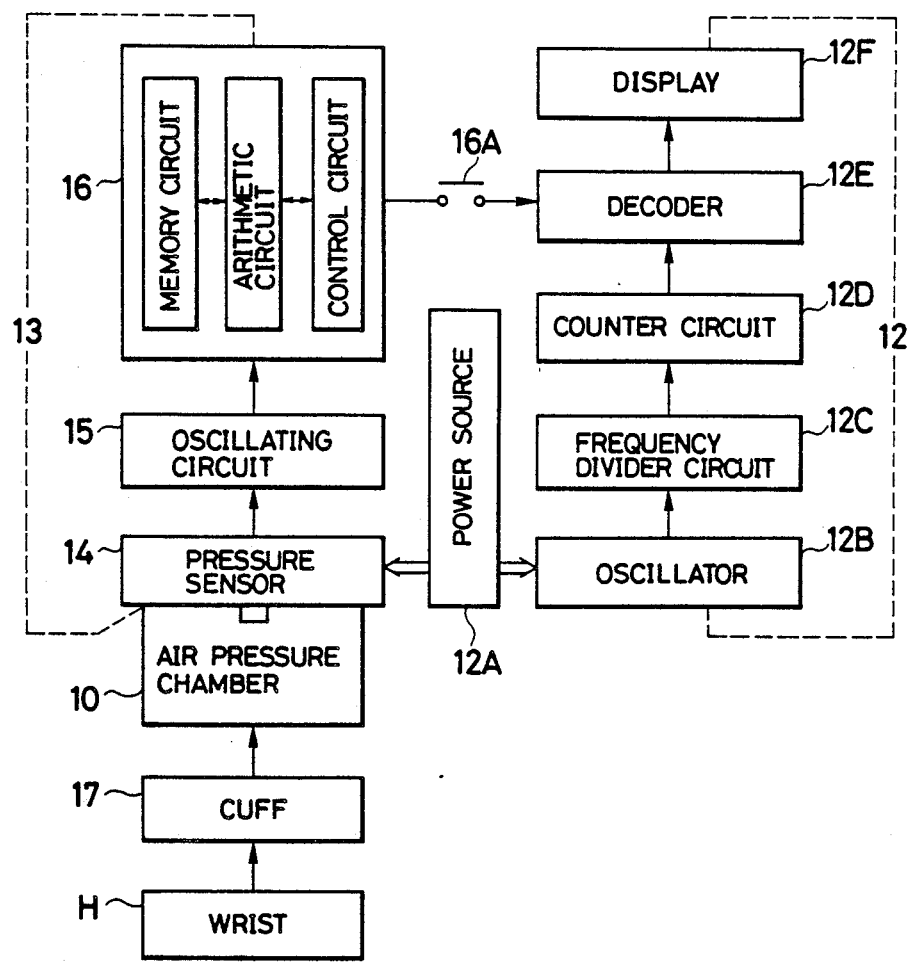
FIG. 4 is a block circuit diagram illustrating the relationship between a digital display device and a blood pressure measuring device in the blood pressure measuring unit.

FIG. 4 is a block circuit diagram showing the relationship between the blood pressure measuring device 13 and the digital display device 12.

The digital display device 12 has the same construction as in the case of an ordinary digital timepiece. That is, an ordinary battery is used for a power source 12A. On the other hand, a crystal oscillator is used for an oscillator 12B. A frequency divider circuit 12C is intended to divide the pulse generated from the oscillator 12B, into a cyclic period corresponding to that of a timepiece. A counter circuit 12D counts in units of seconds, minutes and hours the input signals supplied from the frequency divider circuit 12C. A decoder 12E supplies, in accordance with the numeric values inputted from the counter 12D, a command signal to the display 12F to cause the same 12F to specify the respective contents in its seven-segment digit configuration section.

Thus, display is made of the time numerals on the display 12F.

The blood pressure measuring device 13 is constructed as follows. When the cuff 17 is brought into intimate contact with the wrist H, the pulsatory motion of blood vessels causes the variation in level of the air pressure within the cuff 17. This variation is sensed, by the pressure sensor 14, as the variation in level of the air pressure within the air pressure chamber 10.

An electrostatic variable capacitor is used for the pressure sensor 14. In case of a said pressure sensor comprising, for example, two flat sheets of crystal which have an insulating material member interposed therebetween and across which a voltage is applied, the frequency of oscillations made by the crystal sheets is varied due to the variation in level of the air pressure in the air pressure chamber 10. Electrostatic capacities sensor 14 may be of the diaphragm type as is known in the art. When the pressure sensor 14 of such construction is connected to the oscillating circuit 15, therefore, this circuit 15 operates to convert the signals indicative of the variation in oscillation frequency generated from the pressure sensor 14 into digital signals to supply them into the processor 16.

The processor 16 subjects to its computations based on the data stored beforehand in a memory circuit the signals indicative of oscillation frequency which have been generated from the oscillating circuit 15, into numeric blood-pressure values and pulsation number which then are inputted, via a control circuit, into the decoder 12E of the digital display device 12. Selection of the timepiece or the blood pressure measuring device is performed by the switching operation of a switch 16A.

In accordance with the numeric blood-pressure values and pulsation number supplied from the processor 16, the decoder 12E causes the seven segment display section to operate for making its digital display.

As described above, the invention permits the wrist band 7 to be worn on a wrist, thereby making the blood pressure measuring unit always portable in the same manner as in a wrist watch. Normally, the air in the cuffs 17, 17 is drawn off by opening the discharge valve 18, whereby the unit can be used as a wrist watch.

When it is desired to measure the blood pressure, the air bag 9B of the pump device 9 is repeatedly pushed several times by use of a finger top. By so doing, the suction valve 9D and discharge valve 9F operate so as to cause air to be filled into the air pressure chamber 10 and the cuffs 17, 17 allowed to communicated therewith. That is, the time display as of a wrist watch is stopped beforehand by operation of the switch 16A, whereby the numeric blood pressure values are instead displayed on the display section 12F.

The numeric blood-pressure values are displayed such that, as shown in FIG. 1, a maximum blood pressure value, minimum blood pressure value, etc. are sequentially displayed from the left side. Adjustment of the air pressure in the cuffs 17, 17 can freely be made through operations of the pump 9 and the discharge valve 18.

After completion of the blood-pressure measuring operation, the switch 16A is operated to change over the measuring operation to the timepiece operation. Then, the discharge valve 18 is opened. As a result, the air in the cuffs 17, 17 is discharged. Thus, the blood-pressure measuring unit can be used as an ordinary wrist watch.

Since the blood pressure measuring unit of the invention can always be worn on a user's wrist, it is possible for the user to measure his blood pressure during his conferences, trips, working hours, or games as well, so as to control his health. Particularly, since those persons who suffer from high blood pressure can adequately check a rise in blood pressure during their conferences, working hours, etc., they can readily control their blood pressure. Namely, when they have found that their blood pressure has risen up to a level higher than a certain reference level, they can cease to continue their conferences, or suspend the performance of their working operations, waiting for a decline in the blood pressure.

The invention is not limited to the above-mentioned embodiment but permits various changes or modifications to be suitably made. For instance, the display 12F can be made into a construction wherein a section for time display and a section for blood pressure display are arranged in parallel.

Further, the unit can be additionally equipped with a device which is intended for lighting a red lamp or for generating a warning sound when the user's blood pressure has increased up to a reference high-blood-pressure of, for example, 180.

Figure 5:
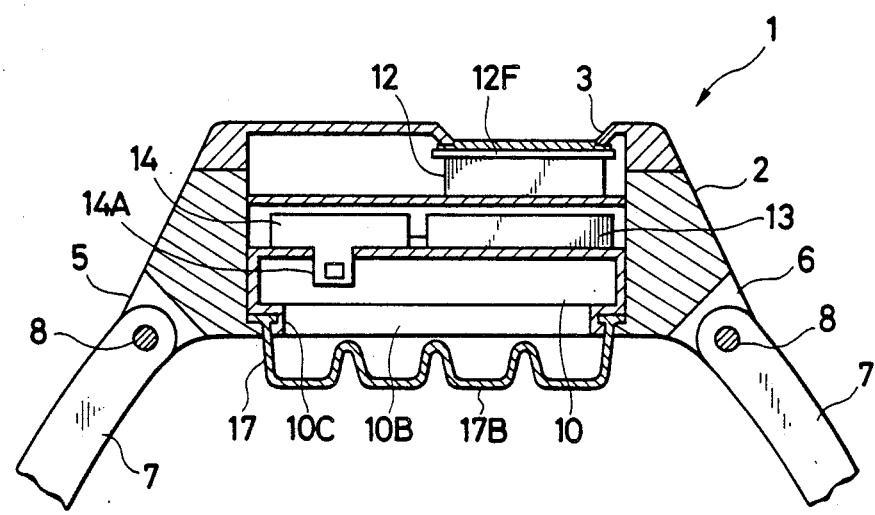
FIG. 5 is a sectional view of a second embodiment of the present invention.

FIG. 5 is a sectional view showing a second embodiment of the invention. In FIG. 5, the members, portions or sections which are the same, or the same in function, as in the preceding first embodiment are denoted by like reference numerals.

This second embodiment differs from the first-mentioned embodiment in that the cuff 17 is mounted on the underside of the air pressure chamber 10. That is, an opening portion 10B is provided at the underside of the air pressure chamber 10, whereby a cap-shaped cuff 17 is fitted over a rim 10C thereof, the cuff 17 being formed with a plurality of dome-like elevations 17B, 17B.

In this second embodiment, the cuff 17 is brought into contact with the inside surface (the portion generally used to measure the pulsation) of a user's wrist. As a result, the expansions and contractions of the blood vessels can be directly sensed by means of the cuff 17. Besides, the cuff 17 can be made small in size. Besides, the unit has an advantage in terms of manufacture since it is unnecessary to mount the cuff 17 on the inner surface of the wrist band 7. Generally, the blood pressure is measured by winding the cuff around the upper part of an arm. This is because it is preferable to measure on a portion of the body nearer to the heart. According to the present invention, since the blood pressure is so arranged as to be measured on a wrist, the values corresponding to the difference between the values measured on the upper portion of arm and those measured on a wrist are stored beforehand in the processor 16. Accordingly, even when the measurement is made on a wrist, it is possible to display, on the display section, the numeric blood-pressure values approximate to those obtained when the blood pressure has been measured on the upper arm portion.

According to the invention, since the pressure sensor is constructed using a variable capacitor, the variation in oscillation frequency can directly be converted by the oscillating circuit into digital signals. Thus, it is possible to miniaturize the blood pressure measuring device and, hence, the blood pressure measuring unit.

The present invention has the following effects or advantages.

(A) since the blood pressure measuring unit of the invention is arranged such that the variation in pressure of the blood vessels in a user's wrist is changed into a variation in air pressure within the cuff and the air pressure chamber which is sensed by the pressure sensor, the unit can be made very small in size, so that it can at all times be carried by a user in a state wherein it is worn on his wrist as in the case of a wrist watch.

(B) Since the digital display device can concurrently be used as a digital watch device as well, the unit can be made a portable blood pressure measuring unit concurrently serviceable as a wrist watch as well. And, (C) Since the unit can at all times be worn on a user's wrist, a person who is high in blood pressure can measure his blood pressure as the necessity arises even in the course of his working operation, thereby making control of his own blood pressure.

What is claimed is:

1. A blood pressure measuring unit of the type which can be worn about the wrist of a user, comprising:

a display device including a digital time displaying watch device;

wrist band means for fitting about the wrist of a user;

casing means secured to said wrist band means for holding at least said display device;

an air pressure chamber secured to said casing means for holding air at a pressure that is greater than atmospheric pressure;

means for supplying compressed air to said pressure chamber;

cuff means for contacting the wrist of a user, formed of resilient material and in communication with said air pressure chamber, said cuff means having a first substantially flat outer surface in contact with an inside surface of said wrist band means, and an inner surface adapted to contact the wrist of a user;

means for sensing the pressure within said air pressure chamber by using an electrostatic variable capacitor formed of flat sheets of capacitive material; and means responsive to said pressure sensing means for calculating the blood pressure of a user, and for supplying such information to said display means so that it may be displayed.

2. A blood pressure measuring unit as claimed in claim 1 wherein said air pressure chamber is formed with openings at both ends thereof, to which said cuff means is connected so as to be in communication therewith.

3. A blood pressure measuring unit as claimed in claim 1 wherein said air pressure chamber is formed, at a lower end surface thereof, with an opening over which said cuff means is fitted.

4. A blood pressure measuring unit as claimed in claim 1 wherein said pressure sensing means is an electrostatic variable capacitor.

5. A blood pressure measuring unit as claimed in claim 1, wherein said air pressure chamber is formed with openings at both ends thereof, to which said cuff means is connected so as to be in communication therewith.

6. A blood pressure measuring unit as claimed in claim 1, wherein said air pressure chamber is formed with openings at both ends thereof, to which said cuff means is connected so as to be in communication therewith.

7. A blood pressure measuring unit as claimed in claim 1, wherein said air pressure chamber is formed, at a lower end surface thereof, with an opening over which said cuff means is fitted.

8. A blood pressure measuring unit as claimed in claim 1, wherein said air pressure chamber is formed, at lower end surface, with an opening over which said cuff means is fitted.

* * * * *